US011215145B2

(12) United States Patent
Duez et al.

(10) Patent No.: US 11,215,145 B2
(45) Date of Patent: Jan. 4, 2022

(54) SYSTEM AND METHOD FOR INJECTING AN AQUEOUS SOLUTION ON-BOARD A VEHICLE

(71) Applicant: Plastic Omnium Advanced Innovation and Research, Brussels (BE)

(72) Inventors: Laurent Duez, Uccle (BE); Arthur Relave-Noiray, Brussels (BE)

(73) Assignee: Plastic Omnium Advanced Innovation and Research, Brussels (BE)

( * ) Notice: Subject to any disclaimer, the term of this patent is extended or adjusted under 35 U.S.C. 154(b) by 134 days.

(21) Appl. No.: 16/608,942

(22) PCT Filed: May 4, 2018

(86) PCT No.: PCT/EP2018/061449
§ 371 (c)(1),
(2) Date: Oct. 28, 2019

(87) PCT Pub. No.: WO2018/202825
PCT Pub. Date: Nov. 8, 2018

(65) Prior Publication Data
US 2020/0056565 A1    Feb. 20, 2020

(30) Foreign Application Priority Data

May 4, 2017    (EP) .................................. 17305497

(51) Int. Cl.
*F02B 47/02* (2006.01)
*F02M 25/022* (2006.01)
(Continued)

(52) U.S. Cl.
CPC ........... *F02M 25/0224* (2013.01); *A61L 2/10* (2013.01); *C02F 1/325* (2013.01); *F02M 25/028* (2013.01);
(Continued)

(58) Field of Classification Search
CPC .... C02F 1/325; C02F 1/32; C02F 2201/3222; F02M 25/0224; B67D 2210/00015
(Continued)

(56) References Cited

U.S. PATENT DOCUMENTS 5,709,799 A * 1/1998 Engelhard ............... C02F 1/325
                                                    210/748.1
6,090,281 A * 7/2000 Buckner .................... C02F 1/36
                                                    210/205
(Continued)

FOREIGN PATENT DOCUMENTS

DE   10 2008 022 406 A1   11/2009
EP      2 481 711 A1       8/2012
(Continued)

OTHER PUBLICATIONS

International Search Report dated Jun. 11, 2018 in PCT/EP2018/061449 filed on May 4, 2018.

*Primary Examiner* — Long T Tran
*Assistant Examiner* — James J Kim
(74) *Attorney, Agent, or Firm* — Oblon, McClelland, Maier & Neustadt, L.L.P.

(57) ABSTRACT

A vehicle system includes a tank for storing an aqueous solution; and a UV light decontamination module configured for decontaminating aqueous solution stored in the tank. The UV light decontamination module is arranged in a wall of the tank. The UV light decontamination module includes a light source compartment which is accessible from an external area outside of the tank; and a light transmission member configured to transmit UV light from the light source compartment to a liquid space in fluid communication with aqueous solution stored in the tank. The light source compartment includes a light source to emit UV light through the light transmission member to the liquid space.

24 Claims, 4 Drawing Sheets

(51) Int. Cl.
*A61L 2/10* (2006.01)
*C02F 1/32* (2006.01)
*F02M 25/028* (2006.01)
*C02F 103/02* (2006.01)

(52) U.S. Cl.
CPC ...... *F02M 25/0222* (2013.01); *A61L 2202/11* (2013.01); *C02F 2103/02* (2013.01); *C02F 2201/322* (2013.01); *C02F 2201/3222* (2013.01); *C02F 2201/3228* (2013.01)

(58) Field of Classification Search
USPC .................................................. 123/25 A
See application file for complete search history.

(56) References Cited

U.S. PATENT DOCUMENTS

| | | | | |
|---|---|---|---|---|
| 6,139,726 A | * | 10/2000 | Greene | ............... C02F 9/005 210/175 |
| 6,764,594 B2 | * | 7/2004 | Lee | ............... A47J 31/605 210/104 |
| 8,618,522 B2 | * | 12/2013 | McKinney | ............... C02F 1/325 250/504 R |
| 9,090,490 B2 | * | 7/2015 | Lydic | ............... C02F 1/325 |
| 2002/0162969 A1 | * | 11/2002 | Reed | ............... A61L 2/10 250/432 R |
| 2005/0000911 A1 | | 1/2005 | Thorpe | |
| 2009/0095691 A1 | | 4/2009 | Thorpe | |
| 2012/0311999 A1 | * | 12/2012 | Hodgson | ............... F01N 3/2066 60/295 |
| 2014/0202948 A1 | * | 7/2014 | Li | ............... C02F 1/008 210/251 |
| 2015/0360924 A1 | * | 12/2015 | Orita | ............... C02F 1/78 222/190 |
| 2018/0128212 A1 | * | 5/2018 | Burak | ............... F02M 25/0224 |

FOREIGN PATENT DOCUMENTS

| | | |
|---|---|---|
| EP | 2 966 025 A1 | 1/2016 |
| KR | 10-2010-0051607 | 5/2010 |
| WO | WO 2004/099532 A1 | 11/2004 |
| WO | WO 2013/155283 A1 | 10/2013 |
| WO | WO 2016/085385 A1 | 6/2016 |
| WO | WO 2016/177556 A1 | 11/2016 |

* cited by examiner

SYSTEM AND METHOD FOR INJECTING AN AQUEOUS SOLUTION ON-BOARD A VEHICLE

CROSS-REFERENCE TO RELATED APPLICATIONS

This application is a United States national stage application of International Application No. PCT/EP2018/061449, filed May 4, 2018, which designates the United States, and claims priority to European Patent Application No. 17305497.4, filed May 4, 2017, and the entire contents of each of the above applications are hereby incorporated herein by reference in entirety.

FIELD OF INVENTION

The invention relates to a vehicle system for storing an aqueous solution, preferably demineralised water, on-board a vehicle, and in particular to a vehicle system for injecting an aqueous solution into an air intake upstream of a combustion chamber or directly in the combustion chamber.

BACKGROUND

It is known to inject water into an air intake upstream of a combustion chamber or directly in the combustion chamber, when the load of the engine of the vehicle is high. By injecting water in the air stream, the air is cooled down, resulting in a higher density and hence more air per volume unit, enhancing the combustion. In that manner more power is obtained, i.e. the performance is boosted.

The water for injection needs to be stored on-board the vehicle, typically for a longer period of time, before all the water has been used for injection. It is known to add additives to the water to maintain the water in a suitable condition. However, such additives may hinder a good operation of the combustion chamber and may damage the fuel injector of the combustion chamber.

SUMMARY

It is an object of exemplary embodiments of the invention to provide a vehicle system for storing an aqueous solution on-board a vehicle, which is capable of storing an aqueous solution in suitable conditions for a longer period of time. More in particular, it is an object of embodiments of the invention to provide a vehicle system which can be used with various types of aqueous solutions, including drinking water and water from natural sources containing bacteria and algae.

According to a first aspect there is provided a vehicle system comprising a tank for storing an aqueous solution; and a UV light decontamination module configured for decontaminating aqueous solution stored in the tank. The UV light decontamination module is arranged in a wall of the tank. The UV light decontamination module comprises a light source compartment which is accessible from an external area outside of the tank; and a light transmission member configured to transmit UV light from the light source compartment to a liquid space in the tank or in a liquid compartment in fluid communication with the tank. The light source compartment comprising a light source configured and arranged to emit UV light through the light transmission member to the liquid space.

By subjecting the aqueous solution to UV light, bacteria and algae can be inactivated in order to decontaminate the aqueous solution. In that manner the aqueous solution can be stored in suitable conditions on-board a vehicle for a longer period of time without the need for special additives. By mounting the UV light decontamination module in a wall of the tank it can be easily added in any type of tank. Further, by providing the UV light decontamination module with a light source compartment which is accessible from an external area outside of the tank, the light source can be easily electrically connected and any maintenance to the UV light decontamination module can be easily performed. The emitted light can be effectively transmitted to the aqueous solution in the liquid space through the light transmission member.

In the context of the present invention the term "liquid space" may be a portion of the volume delimited by the walls of the tank, or may be a space delimited by the walls of a liquid compartment in fluid communication with the tank so that aqueous solution in the tank can flow to the liquid compartment. It is noted that the liquid compartment may be located either completely within the main volume of the tank, or partially or fully outside of the main volume of the tank.

In a preferred embodiment, the vehicle system comprises a vibration absorbing part. Preferably, the light source is arranged in the light source compartment using a vibration absorbing part such that vibrations of the tank are at least partially absorbed in the vibration absorbing part. In that manner the light source will be adequately protected against vibrations inherent to vehicle systems.

In an exemplary embodiment the vibration absorbing part comprises an elastically deformable part which is compressed between the light source and a wall delimiting the light source compartment. Preferably the compression of the elastically deformable material, in a compression direction, is between 5% and 70%, more preferably between 10% and 60%. The elastically deformable part may be compressed over e.g. a distance of 2 to 10 mm. The elastically deformable part may be made of a plastic material e.g. a plastic cellular foam material or a rubber. The vibration absorbing part may be made entirely or partially of the elastically deformable material. The use of such materials is a convenient, robust and compact solution to absorb the vibration energy. The elastically deformable material may be applied e.g. by overmoulding a plastic material over a support, such as a PCB, of the light source; or by potting a resin material such as an epoxy rubber over the support of the light source. Preferably, the resin material has a thermal conductivity at atmospheric pressure and 293K which is higher than 1 $Wm^{-1}K^{-1}$. In that manner heat generated by the light source can be conducted to the external area outside of the tank. It is noted that other means may be added to enhance the transfer of heat out of the light source compartment.

In an exemplary embodiment the UV light decontamination module further comprises a liquid compartment in fluid communication with aqueous solution in the tank. The liquid space is formed in the liquid compartment. The liquid compartment is separated from the light source compartment by a wall comprising the light transmission member or by the light transmission member itself. By providing a liquid compartment the emitted UV light may be contained in the liquid compartment such that the walls of the tank itself do not need to be made from a UV light resistant material. In that manner only the UV light decontamination module can be made of a UV light resistant material.

Preferably, the liquid compartment is provided with at least one inlet and at least one outlet for receiving and discharging aqueous solution from and to the tank, respec- 
tively. In that manner a determined flow path through the UV light decontamination module can be created, resulting in a controlled decontamination of the aqueous solution in the tank.

Preferably the volume of the liquid compartment is between 6000 mm$^3$ and 20.000 mm$^3$, more preferably between 8000 and 160000 mm$^3$. The inventors have found that with such a small, compact compartment, using a typical flow rate of between 5 and 15 l/h, for a tank with a volume between 5 and 15 l a good decontamination can be achieved.

According to a second aspect of the invention there is provided a vehicle system comprising: a tank for storing an aqueous solution; a UV light decontamination module configured for decontaminating aqueous solution stored in the tank; said UV light decontamination module being arranged in a wall of the tank, and said UV light decontamination module comprising: a light source compartment; and a light transmission member configured to transmit UV light from the light source compartment to a liquid space in a liquid compartment in fluid communication with the tank; said light source compartment comprising a light source configured and arranged to emit UV light through the light transmission member to the liquid space (L). The liquid compartment is provided with at least one inlet and at least one outlet for receiving and discharging aqueous solution from and to the tank, respectively. Preferably, the volume of the liquid compartment is between 6000 mm$^3$ and 20000 mm$^3$.

According to this aspect the light source compartment may or may not be accessible from an external area outside the tank. The light source compartment may be located within the volume of the tank, wherein the connection wires of the light source extend in a passage of the UV light decontamination module, through a wall of the tank.

Preferably, the vehicle system comprises a vibration absorbing part adapted to absorb vibrations; said vibration absorbing part comprising an elastically deformable part located between the light source and a wall delimiting the light source compartment. The vibration absorbing part may be implemented as described above. Preferably, the elastically deformable part is compressed, and the compression is between 5% and 70%, more preferably between 10% and 60%.

Preferably, the UV light decontamination module comprises the liquid compartment in fluid communication with the tank, wherein the light transmission member or a wall comprising the light transmission member separates the liquid compartment from the light source compartment. Preferably, the volume of the tank is between 5 and 15 l; wherein preferably the vehicle system is configured to generate a flow rate between 5 and 15 l/h in the liquid compartment.

The features described below are preferred features which may be combined with both the first and second aspect of the invention.

According to a preferred embodiment, the liquid compartment is located inside the tank.

According to an exemplary embodiment, the light source comprises at least one LED source.

According to an exemplary embodiment, the light source compartment comprises a fan configured for removing heat generated by the light source.

According to an exemplary embodiment, the light source compartment comprises a heat sink configured for removing heat generated by the light source.

According to an exemplary embodiment, the vehicle system further comprises an injector, and the vehicle system is configured to pump aqueous solution through the liquid compartment whilst at the same time pumping aqueous solution to the injector. Alternatively or in addition, the vehicle system is configured to be controlled to be in an injection mode or in a bio-decontamination mode, wherein the vehicle system is configured for pumping aqueous solution through the liquid space in the bio-decontamination mode and for pumping aqueous solution to the injector in the injection mode.

According to an exemplary embodiment a housing of the UV light decontamination module is welded to a wall of the tank. For example, the housing of the UV light decontamination module may be provided with a connecting flange welded to a peripheral portion of a wall of the tank, said peripheral portion surrounding an opening in a wall of the tank.

According to an exemplary embodiment the UV light decontamination module comprises a tube-like section extending through a wall of the tank. The tube-like section may be connected to the wall of the tank, e.g. by welding or may be an integral part of the tank. The tube-like section has a first end located in the tank and a second open end located outside of the tank. The light transmission member is sealingly mounted between the first and the second end, so that the liquid compartment is located between the light transmission member and the first end, and the light source compartment is located between the light transmission member and the second open end. Such a configuration provides a compact and robust module which can be easily arranged and integrated in a wall of the tank.

The first end may be an open end or a closed end. When the first end is an open end it may be closed by an internal cap. It is preferred to have a more or less closed liquid compartment (with the exception of the at least one inlet and outlet) in order to avoid that UV light is emitted in the tank. Preferably an inlet from the tank to the liquid compartment is provided in the tube-like section or in the internal cap and an outlet from the liquid compartment to the tank is provided in the tube-like section or in the internal cap.

Also, the second open end may be closed by an external cap. By providing an external cap the components in the light source compartment can be protected against dirt and humidity. Furthermore, it can be ensured that the light source does not fall out of the light source compartment. It is noted that the vibration absorbing part may fulfil all or a part of those functions, especially when a potting material is applied around a portion of the light source. However, generally is it preferred to also provide an external cap.

According to an exemplary embodiment, the vehicle system further comprises a pump unit, preferably at least partially located inside the tank, wherein the UV light decontamination module is arranged so that the pump unit provides a flow of aqueous solution through the liquid space adjacent the light transmission member. In that manner a continuous flow of aqueous solution in the liquid space can be ensured, resulting in an improved decontamination. Hence, the aqueous solution of the tank can be treated continuously with UV light when the pump unit is activated whilst the pump unit may at the same time be used for pumping aqueous solution to an injector. Alternatively the pump unit may be arranged and controlled to be in an injection mode or in a bio-decontamination mode, wherein the pump unit is used for pumping aqueous solution through the liquid space adjacent the light transmission member in the bio-decontamination mode and for pumping aqueous solution to the injector in the injection mode.

By arranging the pump unit at least partially in the tank, a compact system is obtained. Furthermore, only one line (the feed line) is required from the tank (which may be located e.g. in the back of the car) to the injector (which is typically located close to the engine). It is noted that other lines may be provided but this is not required.

In an embodiment the pump unit is arranged in a module mounted in an opening of a wall of the tank. The pump unit may be arranged either inside the tank or at an external side of the module on the outside of the tank, or partially inside and partially outside of the tank. By arranging the pump in a module mounted in an opening in the tank a compact system is obtained which can be easily assembled.

According to an exemplary embodiment the pump unit is integrated in the UV light decontamination module. In other words, a single module is provided which is integrated in an opening of the wall of the tank, implementing both the function of pump and UV light decontamination.

According to an exemplary embodiment the vehicle system further comprises an injector and a feed line connecting an outlet of the pump unit to the injector such that aqueous solution from the tank can be pumped to the injector; and a return line connected to the outlet of the pump unit. The return line is directed towards the liquid space adjacent the light transmission member. The end of the return line may be connected to an inlet of the liquid compartment or may be arranged near the inlet of the liquid compartment. If no liquid compartment is present, the end of the return line may be arranged in or close to the liquid space, e.g. at a distance from the light transmission member which is smaller than 10 cm, preferably smaller than 5 cm. In that manner the return flow is directed to the liquid space adjacent the light transmission member.

According to an exemplary embodiment the UV light decontamination module may further comprise any one or more of the following components: a heater, a level sensor, a quality sensor, a filter, a bowl defining a fluid compartment in the tank.

According to an exemplary embodiment the tank has a bottom wall, a top wall and a sidewall connecting the bottom wall with the top wall, wherein the UV light decontamination module is arranged in the bottom wall, wherein, in the mounted position of the tank, the bottom wall corresponds to the lowest face of the tank. Thereby, the UV light decontamination module can be arranged below the minimum filling liquid level of the tank, and will not normally "run out of" aqueous solution.

According to an exemplary embodiment, the light transmission member is a transparent member, e.g. a member made of a quartz, fused silica, or fluorinated ethylene propylene plastic. In another embodiment the light transmission member may comprise a lens element to direct the emitted UV light in an improved manner to the liquid space, e.g. a lens configured to converge the emitted UV light to the space where it is needed.

Optionally an inner wall of the liquid compartment may be provided with a reflector such as a reflective coating configured for reflecting UV light emitted by the at least one LED source. Alternatively the material of the walls delimiting the liquid compartment may be made of a material reflecting UV light. In that manner the UV light decontamination may be further enhanced.

According to an exemplary embodiment the vehicle system further comprises a jet pump having a suction inlet, a pressure inlet and an outlet. The pump unit may then be connected for pumping aqueous solution along a jet flow path from the tank through the pump unit, through the pressure inlet of the jet pump to the outlet of the jet pump.

In a possible embodiment the outlet may be arranged for directing aqueous solution to the liquid space adjacent the light transmission member. The suction inlet of the jet pump may then be arranged for drawing aqueous solution from another part of the tank. The UV light decontamination module is then arranged to operate on aqueous solution flowing out of the jet flow path.

According to a further embodiment, the suction inlet of the jet pump may be arranged for sucking aqueous solution out of the liquid space adjacent the light transmission member. The outlet of the jet pump may then be arranged for returning aqueous solution in the tank. The UV light decontamination module is then arranged to operate on aqueous solution flowing to the suction inlet.

Using an embodiment with a jet pump, the flow rates in the liquid space may be increased.

According to an exemplary embodiment the light transmission member is mounted moveably in order to allow for a movement in the direction of the light source compartment in case of freezing of the aqueous solution. For example, the light transmission member may be arranged in a sealing manner using elastically deformable material on both sides of the light transmission member such that a limited movement thereof is possible.

It is noted that the walls that delimit the light source compartment and/or the liquid compartment may be an integral part of the tank. In other words, the UV light decontamination module may be an integral part of the tank.

According to another exemplary embodiment the UV light decontamination module is arranged in the sidewall, in a lower half of the tank, wherein, in the mounted position of the tank, the bottom wall corresponds with the lowest face of the tank. Also an such an embodiment the UV light decontamination module may be arranged below the minimum filling level of the tank, ensuring that it can always operate on the aqueous solution in normal operation.

According to exemplary embodiments the liquid space adjacent the light transmission member of the UV light decontamination device may be arranged in the flow path caused by a pump unit, such as at one of an inlet of the pump unit, at an outlet of the pump unit, in a driving line connecting the outlet of the pump unit to a pressure inlet of a jet pump, at the suction inlet of a jet pump, at the outlet of the jet pump.

Preferably, the aqueous solution contains at least 90% water, more preferably at least 95% water, and most preferably at least 98% water; wherein the aqueous solution is for example demineralized water. For such aqueous solutions a UV light decontamination device will be particularly effective.

The invention is especially advantageous for gasoline cars but may also be useful for diesel cars.

BRIEF DESCRIPTION OF THE FIGURES

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which.

DESCRIPTION OF EMBODIMENTS

Figure 1:
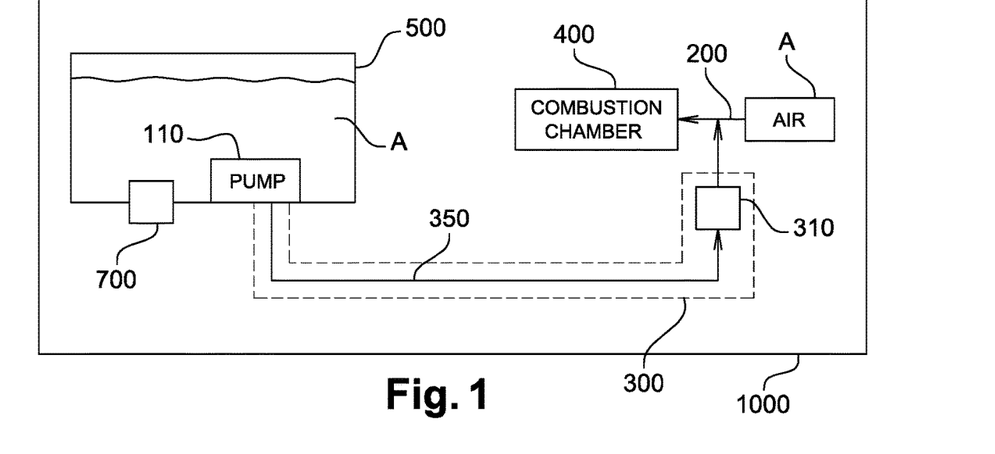
FIG. 1 illustrates schematically an exemplary embodiment of a vehicle system with a UV light decontamination module.

FIG. 1 illustrates a vehicle system 1000 for injecting an aqueous solution A in an air intake line 200 upstream of a combustion chamber 400 of an internal combustion engine (not shown). Alternatively the aqueous solution A may be injected directly in the combustion chamber 400 of the internal combustion engine. More generally the aqueous solution A may be injected anywhere as long as the injection is such that the air A injected in the combustion chamber 400 is cooled. The aqueous solution A is preferably a solution containing at least 90% water, more preferably at least 95% water, and most preferably at least 98% water. The aqueous solution A is e.g. demineralized water. In other embodiments methanol may be added to the aqueous solution A to lower the freezing point.

The vehicle system 1000 in FIG. 1 comprises a tank 500 for storing the aqueous solution A; a pump unit 110 inside tank 500; an air intake line 200 upstream of a combustion chamber 400 of an internal combustion engine; an injection system 300; and a UV light decontamination module 700. UV light decontamination module 700 is configured for decontaminating aqueous solution A stored in tank 500 by emitting UV light on aqueous solution A in tank 500. UV light decontamination module 700 is arranged in a wall of tank 500. UV light decontamination module 700 will be described in more detail referring to FIG. 3 and following. Injection system 300 comprises an injector 310 configured for injecting aqueous solution A in air intake line 200 and a feed line 350 connecting pump unit 110 to injector 310 such that aqueous solution A from the tank 500 can be pumped to the injector 310. By arranging the pump unit 110 in the tank, the injection system 300 can have a simple configuration. Generally it will be sufficient to have one line (feed line 350) between tank 500 and injector 310. Indeed, if pump 110 were to be located close to the injector, a long return line may be required. When the tank 500 is located in the back of the car, the provision of pump unit 110 inside tank 500 enables a significant reduction in required line length compared to prior art solutions where the pump unit is located in the engine compartment. However, other embodiments of the invention may have a pump unit 110 outside tank 500. Pump unit 110 may comprise e.g. a gear pump and a motor (e.g. a BLDC motor).

The vehicle system 1000 may comprise more than one injector 310 configured for injecting aqueous solution A in air intake line 200. In such an embodiment, at least one feed line 350 is arranged for connecting pump unit 110 to the plurality of injectors 310 such that aqueous solution A from the tank 500 can be pumped to the corresponding injectors 310.

Figure 2A:
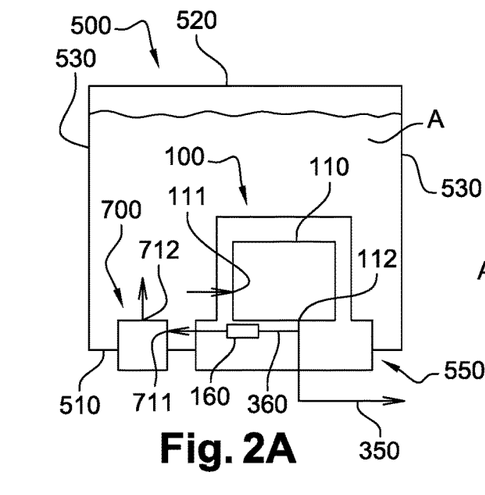
FIGS. 2A, 2B and 2C illustrate three variants of vehicle systems with a UV light decontamination module and a pump unit integrated in a module mounted in a wall of a tank.
Figure 2B:
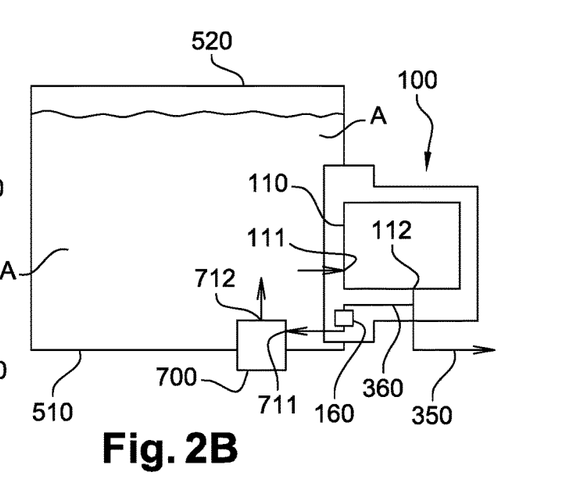
Figure 2C:
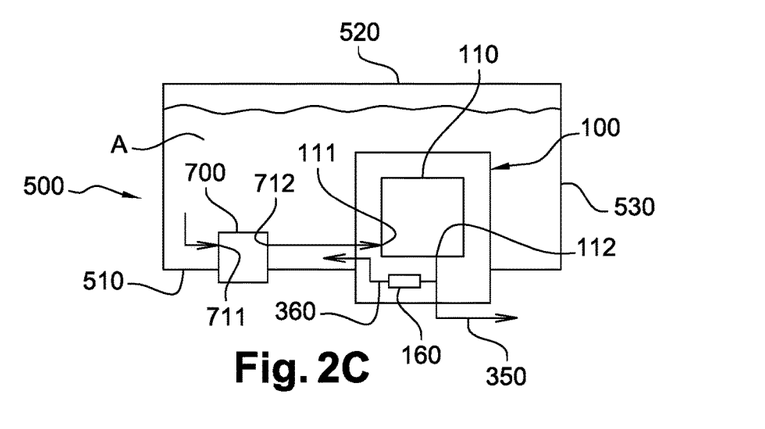

FIGS. 2A and 2C illustrate more detailed exemplary embodiments of tank 500 according to the embodiment in FIG. 1, where pump unit 110 is arranged in a module 100. Module 100 is mounted in an opening 550 in the tank 500. Tank 500 has a bottom wall 510, a top wall 520 and a sidewall 530 connecting the bottom wall 510 with the top wall 520. In the illustrated embodiment opening 550 is arranged in bottom wall 510, wherein, in the mounted position of tank 500, bottom wall 510 corresponds with the lowest face of tank 500.

According to another embodiment illustrated in FIG. 2B, opening 550 may be arranged in sidewall 530. In this exemplary embodiment, pump unit 110 is arranged in a module 100, and pump unit 110 may be arranged fully or partially outside of the tank, see FIG. 2B. It is noted that also in the embodiment of FIGS. 2A and 2C module 100 may protrude out of the bottom wall 510, with pump unit 110 arranged fully or partially outside tank 500.

According to the exemplary embodiments shown in FIGS. 2A-2C, a UV light decontamination module 700 configured for decontaminating aqueous solution A stored in tank 500, is arranged in a wall of tank 500, here in bottom wall 510 of tank 500. However, in other embodiments UV light decontamination module 700 may be arranged in sidewall 530 of tank 500.

According to the exemplary embodiments of FIGS. 2A-2C, module 100 may comprise at least one of the following components (not shown): a heater for heating aqueous solution A in tank 500; a level sensor for sensing the level of the aqueous solution A in tank 500; a quality sensor for measuring the quality of the aqueous solution A in tank 500; a filter, optionally integrated in pump unit 110 for filtering the aqueous solution A before it is transported through feed line 350; a controller for controlling any one or more of the components of the module 100. This controller may also decontamination device 700.

According the exemplary embodiments of FIGS. 2A-2C, there is provided a return line 360 integrated in module 100. Pump unit 110 has an inlet 111 for receiving aqueous solution A from tank 500 and an outlet 112 connected to feed line 350. Return line 360 connects feed line 350 with the interior of tank 500, and may be connected to an inlet 711 of UV light decontamination module 700, see FIGS. 2A and 2B. However, in other embodiments an outlet of return line 360 may be arranged close to a space where UV light is emitted (without being connected to inlet 711 of UV light decontamination module 700), such that a flow is caused in said liquid space. For example, an outlet of return line 360 may be directed towards to the liquid space where UV light is emitted. According to other embodiments, see e.g. FIG. 2C, an outlet 712 of UV light decontamination module 700 may be connected to a suction inlet 111 of pump unit 110, and the inlet 711 may be arranged for receiving aqueous solution A from tank 500. Also for this embodiment it is noted that the suction inlet 111 may be arranged close to a liquid space where UV light is emitted (without being connected to outlet 712 of UV light decontamination module 700), such that a flow is caused in said liquid space. In that regard, it is further noted that UV light decontamination module 700 may comprise a closed liquid compartment with a separate inlet 711 and outlet 712, but may also comprise an open liquid compartment or no liquid compartment at all, see the embodiments of FIG. 3 and following which will be described below. More generally, preferably UV light decontamination module 700 is arranged such that pump unit 110 can cause a flow of aqueous solution A through a liquid space where UV light is being emitted.

Return line 360 may be connected to feed line 350 in module 100. Return line 360 may comprise a check valve 160 in order to regulate the return flow. It is noted that FIGS. 2A-2C are schematic drawings and that inlet 111 is preferably located as low as possible in the tank, and more generally below the minimum filling level. Also inlet 711 of UV light decontamination module 700 is preferably located as low as possible in the tank, and more generally below the minimum filling level.

According to a further embodiment, module 100 with pump unit 110 and UV light decontamination module 700 may be integrated in a single module (not shown).

Figure 3A:
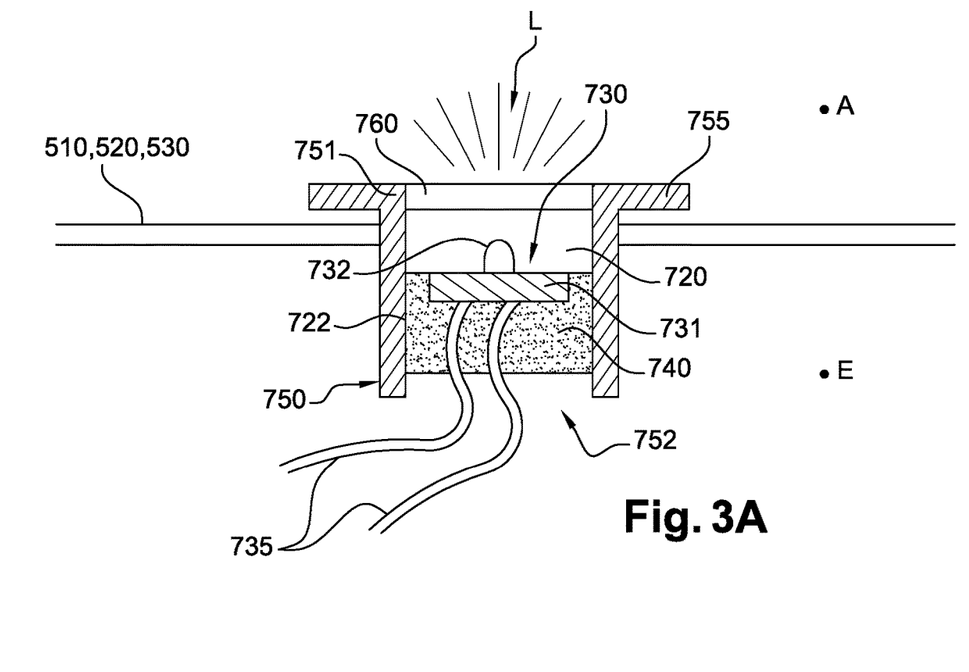
FIGS. 3A and 3B illustrate schematically a cross section of a first and a second exemplary embodiment of a UV light decontamination module, without and with liquid compartment, respectively.
Figure 3B:
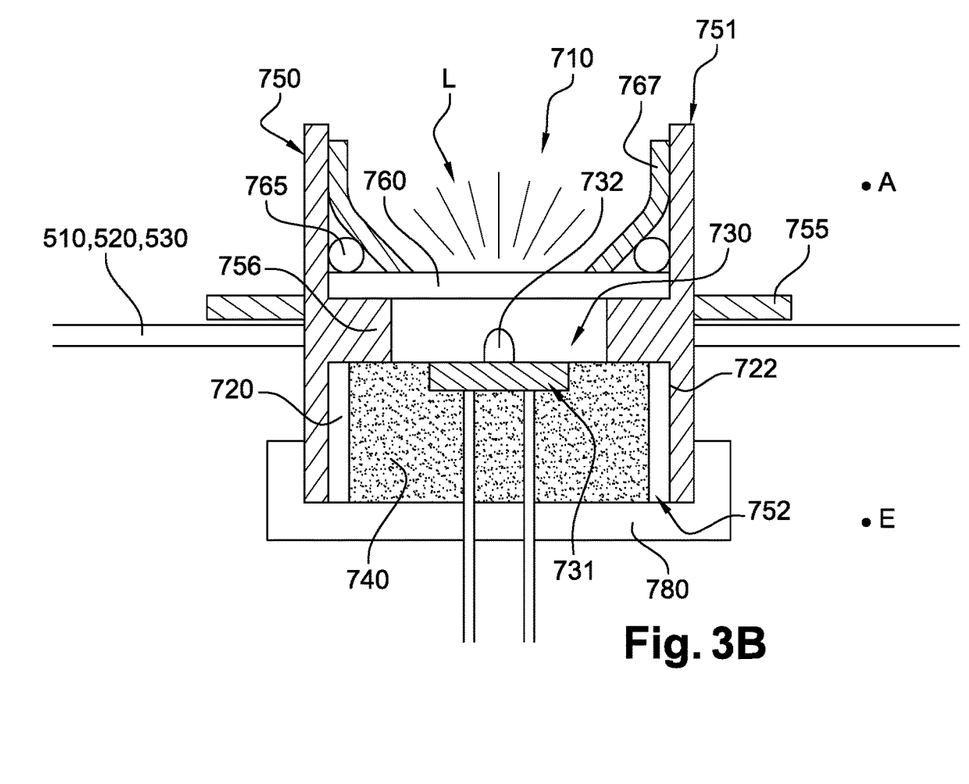

FIGS. 3A and 3B illustrate two exemplary embodiments of a UV light decontamination module 700 configured for decontaminating aqueous solution A stored in a tank with a wall 510, 520, 530, by emitting UV light. UV light decontamination module 700 is arranged in a wall 510, 520, 530 of the tank, and comprises a light source compartment 720 which is accessible from an external area E external to the tank, and a light transmission member 760 configured to transmit UV light from light source compartment 720 to a liquid space L accessible by aqueous solution A stored in the tank. Light source compartment 720 is formed in a housing 750.

Light source compartment 720 comprises a light source 730 configured and arranged to emit UV light through light transmission member 760 to the liquid space L accessible by aqueous solution A stored in the tank. Light source 730 may comprise at least one LED 732, optionally in combination with at least one lens element (not shown). Preferably, the light source 730 comprises a support 731 such as a PCB, on which the at least one LED 732 is mounted. Light source 730 may be connected using connection wires 735.

Light transmission member 760 may be a transparent plate, e.g. a plate made of quartz, fused silica, or fluorinated ethylene propylene plastic. In other embodiments light transmission member 760 may be a lens element configured to converge emitted light to liquid space L. Light transmission member 760 is sealingly mounted in UV light decontamination module 700 such that there is provided a liquid-tight light source compartment 720.

Light source 730 is arranged in light source compartment 720 using a vibration absorbing part 740 such that vibrations of the tank are at least partially absorbed in the vibration absorbing part 740. Preferably vibration absorbing part 740 comprises an elastically deformable material which is compressed between light source 730 and a wall delimiting the light source compartment 720. In the illustrated embodiment the vibration absorbing part 740 is compressed between support 731 of light source 730 and an inner wall 722 delimiting light source compartment 720. Preferably, the elastically deformable material may have a modulus of Young between 0.05 MPa and 3 MPa at atmospheric pressure and at a temperature of 293K.

In the embodiment of FIG. 3B an external cap 780 is provided to close light source compartment 720. Such an external cap 780 will further prevent the light source against dust. External cap 780 may comprise a seal (not shown) such that light source compartment 720 is closed in a sealing manner. In such an embodiment external cap 780 may also compress vibration absorbing part 740. In such an embodiment it is also possible that the vibration absorbing part 740 is only compressed between external cap 780 and a ridge 756 protruding from the inner wall 722. Generally, the elastically deformable material 740 may be compressed in any manner in the light source compartment 720 as long as it can absorb vibrations from the tank. Preferably the compression of the elastically deformable material 740 is between 5% and 70%, more preferably between 10% and 60%. In that manner a good absorption of the vibrations can be achieved.

The vibration absorbing part 400 may be applied by potting a resin material on the support 731. The resin material may have a thermal conductivity at atmospheric pressure and 293K which is higher than 1 $Wm^{-1}K^{-1}$. In that manner heat generated by light source 730 can be thermally conducted through the vibration absorbing part 400 to the external area E outside of the tank.

In the embodiment of FIG. 3B UV light decontamination module 700 further comprises a liquid compartment 710 in fluid communication with aqueous solution A in the tank. Liquid compartment 710 is separated from light source compartment 720 by a wall comprising light transmission member 760. Light transmission member 760 is here a transparent plate supported on ridge 756 and sealingly fixed by seal ring 765 and insert 767 which presses seal ring 765 against an interface between an edge of light transmission member 760 and an inner wall of housing 750. The insert 767 may be a hollow part which is fixed e.g. by screw thread, in housing 750.

Housing 750 of UV light decontamination module is formed by a tube-like section extending through a wall 510, 520, 530 of the tank. An outer wall of housing 750 may be provided with a connecting flange 755 suitable for being welded to the tank material. Alternatively housing 750 may be provided with other means allowing the mounting of the module 700 in an opening in a wall of a tank, such as a bayonet coupling means. Tube-like section 750 has a first end 751 in the tank and a second open end 752 outside of the tank. In the embodiment of FIG. 7A, light transmission member 760 is sealingly mounted at the first end 751. In the embodiment of FIG. 7B, light transmission member 760 is sealingly mounted between the first end 751 and the second end 752, such that liquid compartment 710 is located between light transmission member 760 and first end 751, and the light source compartment 720 is located between the light transmission member 760 and second open end 752.

Preferably UV light decontamination module 700 of FIG. 3A or 3B is arranged in the tank such that a pump unit (not shown) can cause a flow of aqueous solution A through the liquid space L adjacent light transmission member 760. It is noted that the pump unit may be located inside or outside the tank.

As explained in connection with FIGS. 2A-2C, a return line 360 connected to the outlet 112 of the pump unit 110 may be directed towards the liquid space L adjacent the light transmission member 760 or may end in the liquid space L. Preferably the distance between an outlet end of the return line 360 and the light transmission member 760 is smaller than 10 cm, more preferably smaller than 5 cm. Alternatively a suction inlet 111 may be located near or in the liquid space L adjacent the light transmission member 760. In that case, preferably the distance between the suction inlet 111 and the light transmission member 760 is smaller than 10 cm, more preferably smaller than 5 cm.

Figure 4A:
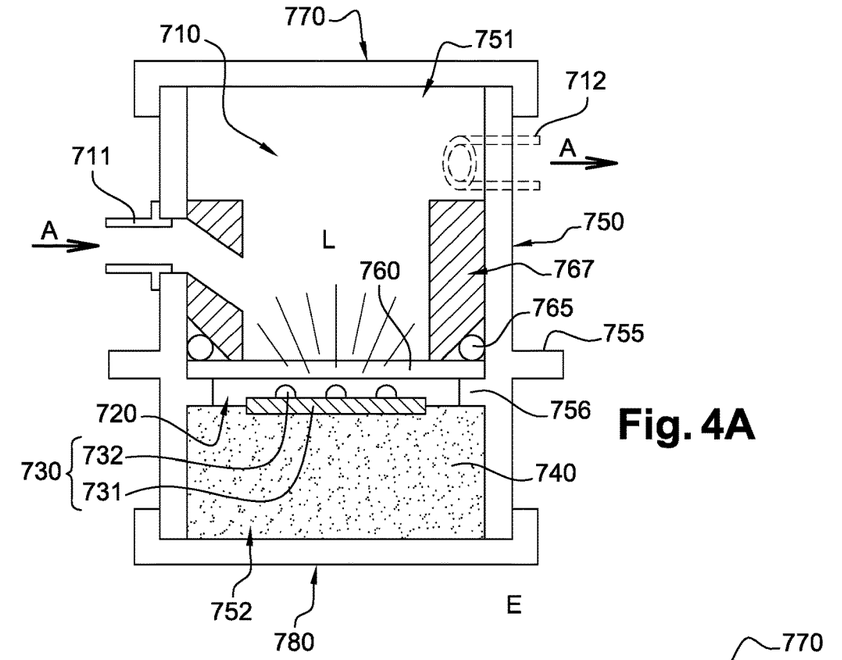
FIGS. 4A and 4B illustrate schematically a cross section and a perspective view of an exemplary embodiment of a UV light decontamination module.
Figure 4B:
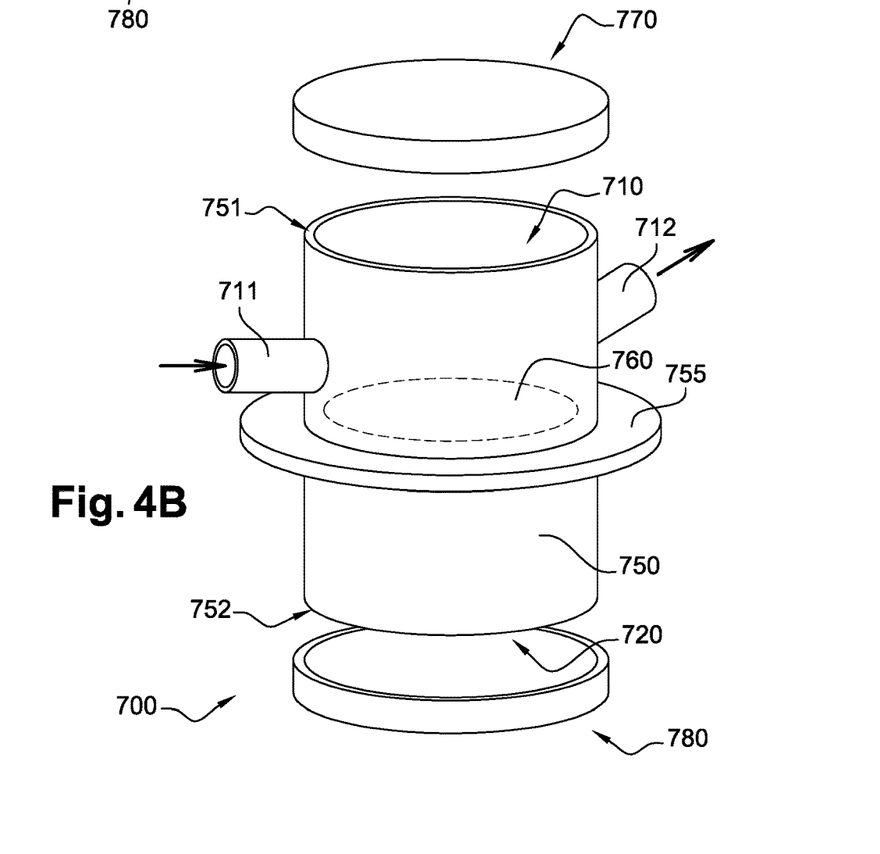

FIGS. 4A and 4B illustrate another exemplary embodiment of a UV light decontamination module 700. The embodiment is similar to the embodiment of FIG. 3B and the same reference numerals have been used to refer to the same or similar components. In the embodiment of FIGS. 4A and 4B the first end 751 of the tube-like housing 750 is an open end 751 closed by an internal cap 770 and the second open end 752 thereof is closed by an external cap 780. An inlet 711 from the tank to the liquid compartment 710 is provided in the tube-like housing 750. Further, an outlet 712 from the liquid compartment 710 to the tank is provided in the tube-like section 750.

Alternatively the inlet 711 and/or the outlet 712 could be provided in the internal cap 770. The inlet 711 and outlet 712 are arranged for receiving and discharging aqueous solution A from and to the tank, respectively. The volume of the liquid compartment 710 may be rather small, e.g. between 6000 mm$^3$ and 20000 mm$^3$, preferably between 8000 and 160000 m$^3$. The inventors have found that for tanks with a volume between 5 and 20 l, when using a flow rate between 5 and 100 l/h, a good decontamination of the aqueous solution A may be obtained.

As explained in connection with FIGS. 2A-2C, the return line 360 connected to the outlet 112 of the pump unit 110 may be connected to the inlet 711 of the liquid compartment 710. Alternatively the suction inlet 111 of the pump unit 110 may be connected to the outlet 712 of the liquid compartment 710.

Optionally, wherein an inner wall of the liquid compartment 710, i.e. an inner side of internal cap 770 and/or an inner wall of tube-like section 750 may be provided with a reflector such as a reflective coating configured for reflecting UV light emitted by light source 730.

Figure 5:
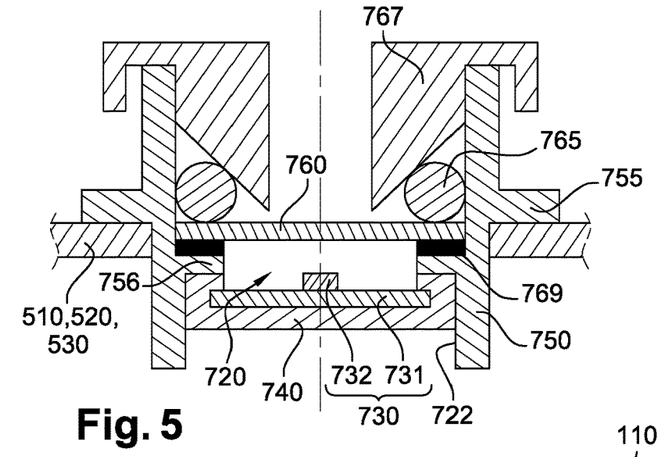
FIG. 5 illustrate schematically a cross section of another exemplary embodiment of a UV light decontamination module.

FIG. 5 illustrates another exemplary embodiment of a UV light decontamination module 700. The embodiment is similar to the embodiment of FIG. 3B and the same reference numerals have been used to refer to the same or similar components. In the embodiment of FIG. 5 the vibration absorbing part 740 surrounds the support 731 over at least a bottom surface thereof and the side edges. The vibration absorbing part 740 is made of an elastically deformable material which is compressed between support 731 of light source 730 and a wall delimiting the light source compartment 720. In the illustrated embodiment the vibration absorbing part 740 is compressed between support 731 of light source 730 and an inner wall 722 delimiting light source compartment 720. Further an elastic material 769 is provided between light transmission member 760 and ridge 756 capable of allowing light transmission member 760 to move slight downward in case of ice formation. Although not illustrated in FIGS. 3A, 3B, 4A and 4B, the skilled person understands that also in those embodiments similar measures may be taken.

Figure 6:
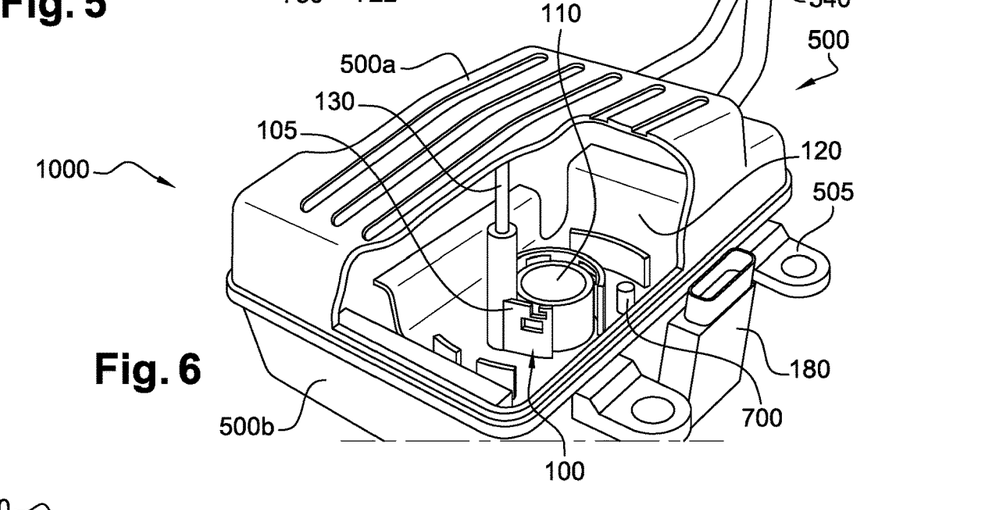
FIG. 6 illustrates a perspective view of an exemplary embodiment of a vehicle system with a tank in which a UV light decontamination module is arranged.

FIG. 6 illustrates an exemplary embodiment of a vehicle system 1000 with a module 100 arranged in an opening of the bottom wall of tank 500, and a UV decontamination module 700 arranged in another opening of the bottom wall of tank 500, in a similar manner as shown in FIGS. 2A and 2C. UV decontamination module 700 may be implemented according to any one of the embodiment described above. Module 100 comprises a compartment 105, and a pump unit 110 arranged in compartment 105. Pump unit 110 may have a suction inlet (not visible) at the lower end of pump unit 110. The outlet (not visible) of pump unit 110 may be located at a lower end of pump unit 110. The suction inlet or the outlet of the pump unit 110 may be connected to the UV decontamination module 700 in any one of the ways. The module 100 may comprise a portion of feed line and a return line including a check valve, as in the embodiment of FIG. 2A or 2C. A heater 120 is provided adjacent cylindrical compartment 105 of module 100. Heater 120 is preferably an electrical heater. In the illustrated embodiment the heater is a flexible electrical heater 120 comprising a flexible sheet with integrated electrical tracks. The flexible heater comprises a central portion intended for extending parallel to a wall of the tank 500, and four flaps which may be attached to tank portions on the inside of the tank. Central portion is provided with an opening through which compartment 105 protrudes. Compartment 105 has a shape which is such that an inner volume is created for receiving the pump unit 110, and a further volume for receiving a level sensor 130.

The tank 500 comprises a bottom shell 500b and a top shell 500a. The flexible electrical heater 120 is arranged in the bottom shell 500b and extends over the bottom wall and a portion of the side wall. Attachment pads 505 may be arranged against a side wall 530 of the tank 500. Further a controller 180 may be provided to control one or more components of the module 100 and of the module 700. The upper shell 500a is provided with a filler pipe 540 for filling the tank 500 with aqueous solution A.

In exemplary embodiments of the invention, preferably, the pump unit 110 may generate a flow of between 5 and 100 l/h through the return line 360. Further, the controller is preferably configured to control pump unit 110 in function of the RPM of the vehicle. When the RPM reaches a predetermined threshold, the pump unit 110 is made to pump with a flow speed within a predetermined range. Although a gear pump is advantageous for use in exemplary embodiments, also other pumps may be used, e.g. a gerotor pump, a turbine pump, a membrane pump, a piston pump.

Figure 7:
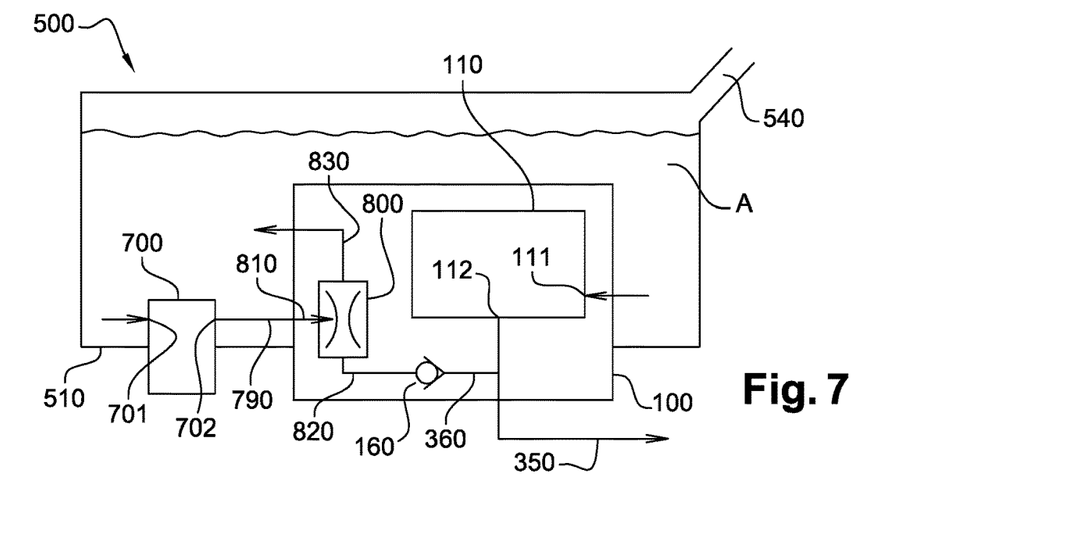
FIG. 7 illustrates schematically a cross section of an exemplary embodiment of a vehicle system with a jet pump.

FIG. 7 illustrates yet another exemplary embodiment of a tank 500 for storing aqueous solution A. A module 100 is arranged in a first opening in a wall of tank 500, and a UV light decontamination module 700 is arranged in a second opening in a wall of tank 500. Tank 500 is provided with a filler pipe 540 for filling tank 500 with aqueous solution A. Module 100 and 700 may be arranged in the respective opening in bottom wall 510 of tank 500, e.g. by welding or by any other suitable connection means, e.g. using a ring-nut system screwed onto a thread on tank 500, or using a closure system of the bayonet type.

Module 100 comprises a feed pump unit 110 and a jet pump 800. Feed pump unit 110 is connected for pumping aqueous solution A from the tank 500 to a feed outlet 112. Feed outlet 112 is intended for being connected to a feed line 350 for injecting aqueous solution A by an injector. Jet pump 800 has a suction inlet 810, a pressure inlet 820 and an outlet 830. Pump unit 110 is further connected for pumping aqueous solution along a jet flow path. The jet flow path extends from an inlet 111 of feed pump unit 110 to an outlet 112 of feed pump unit 110 through a return line 360 between outlet 112 and pressure inlet 820 of jet pump 800, to outlet 830 of jet pump 800. Suction inlet 810 of jet pump 800 is connected to a suction line 790 arranged for receiving aqueous solution from the UV decontamination module 700. Outlet 830 of jet pump 800 is arranged for returning aqueous solution from suction inlet 810 and from pressure inlet 820 to the tank 500. In this way, the aqueous solution being transferred by the jet pump 800 through the suction line 790 is decontaminated by the UV light decontamination device 700.

Alternatively (not shown) the inlet 701 of UV light decontamination module may be connected to outlet 830 of jet pump 800, and suction inlet 811 could then be arranged to suck aqueous solution out of the tank 5. Especially when the tank 500 comprises two compartments, suction inlet 111 may be arranged in a first compartment of the tank 500 and suction inlet 810 may then be arranged in the second compartment.

In alternative embodiments the jet pump 800 in the embodiment of FIG. 7 may be arranged outside of the tank 500.

Whilst the principles of the invention have been set out above in connection with specific embodiments, it is to be understood that this description is merely made by way of example and not as a limitation of the scope of protection which is determined by the appended claims.

The invention claimed is:

1. A vehicle system comprising:
   a tank for storing an aqueous solution;
   a UV light decontamination module configured for decontaminating aqueous solution stored in the tank;
   said UV light decontamination module being arranged in a wall of the tank, and
   said UV light decontamination module comprising:
      a light source compartment which is accessible from an external area outside of the tank; and
      a light transmission member configured to transmit UV light from the light source compartment to a liquid space in a liquid compartment in fluid communication with the tank;
      said light source compartment comprising a light source configured and arranged to emit UV light through the light transmission member to the liquid space;
   wherein the liquid compartment is provided with at least one inlet and at least one outlet for receiving and discharging aqueous solution from and to the tank, respectively,
   wherein the volume of the liquid compartment is between 6000 $mm^3$ and 20000 $mm^3$, and
   wherein the UV light decontamination module comprises a tube-like section extending through the wall of the tank, said tube-like section having a first end in the tank and a second open end outside of the tank, wherein the light transmission member is sealingly mounted between the first and the second end, so that the liquid compartment is located between the light transmission member and the first end, and the light source compartment is located between the light transmission member and the second open end.

2. The vehicle system according to claim 1, comprising a vibration absorbing part adapted to absorb vibrations; said vibration absorbing part comprising an elastically deformable part located between the light source and a wall delimiting the light source compartment.

3. The vehicle system according to claim 2, wherein the elastically deformable part is compressed, and the compression relative to the total length of the elastically deformable part is between 5% and 70%.

4. The vehicle system according to claim 1, wherein the UV light decontamination module comprises the liquid compartment in fluid communication with the tank, wherein the light transmission member or a wall comprising the light transmission member separates the liquid compartment from the light source compartment.

5. The vehicle system according to claim 1, wherein the volume of the tank is between 5 and 15 l; wherein the vehicle system is configured to generate a flow rate between 5 and 15 l/h in the liquid compartment.

6. The vehicle system according to claim 1, wherein the liquid compartment is located inside the tank.

7. The vehicle system according to claim 1, wherein the first end is an open end closed by an internal cap; and/or wherein the second open end is closed by an external cap.

8. The vehicle system according to claim 1, further comprising a pump unit, wherein the UV light decontamination module is arranged such that the pump unit can cause a flow of aqueous solution through the liquid space adjacent the light transmission member.

9. The vehicle system according to claim 8, wherein the pump unit is integrated in the UV light decontamination module.

10. The vehicle system according to claim 8, further comprising an injector and a feed line connecting an outlet of the pump unit to the injector such that aqueous solution from the tank can be pumped to the injector; and a return line connected to the outlet of the pump unit; wherein the return line is directed towards the liquid space adjacent the light transmission member.

11. The vehicle system according to claim 10, wherein the return line is connected to the at least one inlet of the liquid compartment.

12. The vehicle system according to claim 1, wherein the tank has a bottom wall, a top wall and a sidewall connecting the bottom wall with the top wall, wherein the UV light decontamination module is arranged in the bottom wall, wherein, in the mounted position of the tank, the bottom wall corresponds with the lowest face of the tank.

13. The vehicle system according to claim 1, wherein the light transmission member is a transparent member.

14. The vehicle system according to claim 1, wherein the light transmission member is mounted moveably so that it allows a movement in the direction of the light source compartment.

15. A vehicle system comprising:
   a tank for storing an aqueous solution;
   a UV light decontamination module configured for decontaminating aqueous solution stored in the tank;
   said UV light decontamination module being arranged in a wall of the tank, and
   said UV light decontamination module comprising:
   a light source compartment; and
   a light transmission member configured to transmit UV light from the light source compartment to a liquid space in a liquid compartment in fluid communication with the tank;
   said light source compartment comprising a light source configured and arranged to emit UV light through the light transmission member to the liquid space;
   wherein the liquid compartment is provided with at least one inlet and at least one outlet for receiving and discharging aqueous solution from and to the tank, respectively,
   wherein the volume of the liquid compartment is between 6000 $mm^3$ and 20000 $mm^3$, and
   wherein the UV light decontamination module comprises a tube-like section extending through the wall of the tank, said tube-like section having a first end in the tank and a second open end outside of the tank, wherein the light transmission member is sealingly mounted between the first and the second end, so that the liquid compartment is located between the light transmission member and the first end, and the light source compartment is located between the light transmission member and the second open end.

16. The vehicle system according to claim 15, comprising a vibration absorbing part adapted to absorb vibrations; said vibration absorbing part comprising an elastically deformable part located between the light source and a wall delimiting the light source compartment.

17. The vehicle system according to claim 16, wherein the elastically deformable part is compressed, and the compression is between 5% and 70%.

18. The vehicle system according to claim 15, wherein the UV light decontamination module comprises the liquid compartment in fluid communication with the tank, wherein the light transmission member or a wall comprising the light transmission member separates the liquid compartment from the light source compartment.

19. The vehicle system according to claim 15, wherein the volume of the tank is between 5 and 15 l, and wherein the vehicle system is configured to generate a flow rate between 5 and 15 l/h in the liquid compartment.

20. The vehicle system according to claim 15, wherein the liquid compartment is located inside the tank.

21. The vehicle system according to claim 15, wherein the light source comprises at least one LED source.

22. The vehicle system according to claim 15, further comprising an injector, wherein the vehicle system is configured to pump aqueous solution through the liquid compartment whilst at the same time pumping aqueous solution to the injector.

23. The vehicle system according to claim 15, further comprising an injector, wherein the vehicle system is configured to be controlled to be in an injection mode or in a bio-decontamination mode, wherein the vehicle system is configured for pumping aqueous solution through the liquid space in the bio-decontamination mode and for pumping aqueous solution to the injector in the injection mode.

24. The vehicle system according to claim 15, wherein a housing of the UV light decontamination module is welded to a wall of the tank.

\* \* \* \* \*